United States Patent [19]

Muller et al.

[11] 4,145,344
[45] Mar. 20, 1979

[54] BICYCLOMYCIN DERIVATIVES

[75] Inventors: Beat Müller, Reinach; Wilhelm Kump, Biel-Benken; Oskar Wacker, Basel, all of Switzerland

[73] Assignee: Ciba-Geigy Corporation, Ardsley, N.Y.

[21] Appl. No.: 817,314

[22] Filed: Jul. 20, 1977

[30] Foreign Application Priority Data

Aug. 2, 1976 [LU] Luxembourg .................. 75516

[51] Int. Cl.$^2$ ........................................... C07D 498/08
[52] U.S. Cl. ............................. 260/239.3 B; 424/250
[58] Field of Search ................................. 260/239.3 B

[56] References Cited
U.S. PATENT DOCUMENTS 3,873,526   3/1975   Kamiya et al. ................ 260/239.3 B

*Primary Examiner*—Henry R. Jiles
*Assistant Examiner*—Robert T. Bond

[57] ABSTRACT

Bicyclomycin derivatives (i.e. compounds with the skeleton of the 5-methylene-2-oxa-7,9-diazabicyclo[4,2,2]decane) of the formula

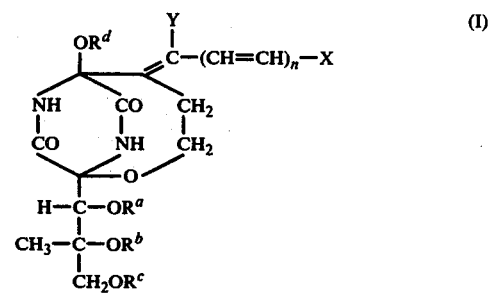

wherein $R^a$ to $R_d$ represent hydrogen atoms or hydroxyl protective groups, X represents a free or functionally modified carboxyl group, a substituted or unsubstituted hydrocarbon radical or a halogen atom, and n is 0 or 1, possess valuable antibiotic properties which are of importance in particular for combating infections caused by Enterobacteriaceae and Proteus species.

10 Claims, No Drawings

BICYCLOMYCIN DERIVATIVES

The present invention relates to bicyclic compounds with the basic skeleton of the 5-methylene-2-oxa-7,9-diazabicyclo[4,4,2]decane of the formula

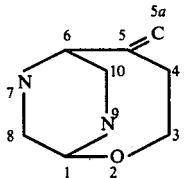

and in particular to derivatives of the bicyclomycin of the formula

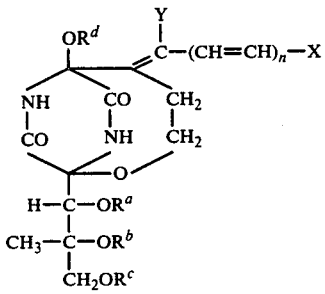

wherein each of $R^a$, $R^b$, $R^c$ and $R^d$ individually represents a hydrogen atom or a hydroxyl protective group $R^1$, or any two of the symbols $R^a$, $R^b$ and $R^c$ together represent a bivalent hydroxyl protective group $R^2$, or these three symbols together represent a trivalent hydroxyl protective group $R^3$, X represents a free or functionally modified carboxyl group, an unsubstituted or substituted monovalent hydrocarbon radical or a halogen atom, Y represents a hydrogen atom or has one of the meanings assigned to X, and n is 0 or 1, and to salts of these compounds, provided they contain salt-forming groups, and also to a process for the manufacture of said compounds and to preparations which contain them and to the use thereof, as well as to therepeutic methods of combating infectious diseases which comprise the use of the said compounds and preparations.

In these compounds, the substituents at two carbon atoms forming a double bond can be in the cis- and trans-configuration, for example the symbol Y in relation to the cyclic portion of the molecule or the 6-hydroxyl group thereof. Unless otherwise specifically stated, each individual double bond can accordingly represent both a mixture of the two isomeric forms and an individual isomer.

For the sake of clarity, the nomenclature of the corresponding compounds throughout the description and the Examples is derived from bicyclomycin[systematic name: 6-hydroxy-5-methylene-1-(1′,2′,3′-trihydroxy-2′-methylpropyl)-2-oxa-7,9-diazabicyclo[4,2,2]decane-8,10-dione] or from 5-norbicyclomycin [systematic name: 6-hydroxy-1-(1′,2′,3′-trihydroxy-2′-methylpropyl)-2-oxa-7,9-diazabicyclo[4,2,2]decane-8,10-dione] as basic substance; the carbon atom of the methylene group in the 5-position is designated 5a.

A hydroxyl protective group $R^1$ is a group which can be replaced by hydrogen, chiefly a monovalent acyl group $Ac^1$, and also a triarylmethyl radical, in particular the trityl radical, a 2-oxaalkyl or 2-oxacycloalkyl group, in particular a 1-butoxyethyl or 2-tetrahydropyranyl group, as well as an organic silyl group as is present for example in tri-lower alkylsilyloxy groups, such as trimethylsilyloxy or dimethyl-tert.-butylsilyloxy groups, or phenyl di-lower alkylsilyloxy or lower alkyldiphenylsilyloxy groups.

A bivalent hydroxyl protective group $R^2$ formed by any two of the symbols $R^a$, $R^b$ and $R^c$ can be the bivalent acyl group $Ac^2$ of an organic dicarboxylic acid, preferably one containing not more than 18 carbon atoms, in particular the oxalyl group. It can also be a carbonyl, thiocarbonyl, sulphonyl or sulphinyl group, but is primarily an acyclic, carbocyclic or carbocyclic-acyclic ylidene radical, preferably one having not more than 18 carbon atoms, as in particular the isopropylidene radical which is bonded to the oxygen atoms in the 2′,3′-position.

A hydroxyl protective group $R^3$ formed by all three symbols, $R^a$, $R^b$ and $R^c$ is in particular an acyclic ylidyne radical, especially a lower alkylidyne radical, for example the ethylidyne radical and preferably the methylidyne radical, which can also carry carbocyclic or heterocyclic hydrocarbon radicals.

Unless stated to the contrary, the term "lower" used throughout this specification to qualify organic groups and radicals means that these contain not more than 7, preferably not more than 4, carbon atoms.

A halogen atom represented by X and/or Y is an iodine, bromine and especially chlorine or fluorine atom.

A functionally modified carboxyl group is in particular an esterified carboxyl group, the cyano group, an unsubstituted or substituted carbamoyl, carbazoyl and amidino group, and also a haloformyl group, such as a bromoformyl and, in particular, chloroformyl, group, and an azidoformyl group.

An esterified carboxyl group is a group in which the hydrogen atom is replaced by an unsubstituted or substituted monovalent hydrocarbon radical. Such a hydrocarbon radical is preferably a lower alkyl radical which can also carry hydroxyl, lower alkoxy, oxo and/or epoxy groups, as well as an unsubstituted or substituted phenyl-lower alkyl radical, in particular a benzyl or phenacyl radical, which can carry in the phenyl moiety halogen atoms, such as chlorine, bromine, iodine and fluorine atoms, lower alkyl radicals, lower alkoxy groups and nitro groups. Examples of particularly preferred esterified carboxyl groups are: methoxycarbonyl, ethoxycarbonyl, propoxycarbonyl, butoxycarbonyl, tert-butoxycarbonyl, 2-hydroxyethoxycarbonyl, 2,3-dihydroxypropoxycarbonyl, 2-methoxyethoxy, 2,3-oxidopropoxycarbonyl, benzyloxycarbonyl, p-chlorobenzyloxycarbonyl, p-nitrobenzyloxycarbonyl, p-methoxybenzyloxycarbonyl, 2-phenylethoxycarbonyl, phenacyloxycarbonyl, p-nitrophenacyloxycarbonyl and p-bromophenacyloxycarbonyl groups.

The nitrogen atoms of the amidino, carbamoyl and carbazoyl group can be substituted by one or two lower alkyl, phenyl or phenyl-lower alkyl radicals. Where the nitrogen atoms are disubstituted, two lower alkyl radicals can also be linked together by a simple C-C bond or by an oxygen, sulphur or unsubstituted or lower alkylated nitrogen atom, and thus together with the nitrogen atom form a saturated nitrogen-containing heterocyclic ring. Examples of such preferred carbamoyl groups are: a lower alkyl or di-lower alkyl group, such as the methylcarbamoyl, ethylcarbamoyl, dimethylcarbamoyl or diethylcarbamoyl group, and also the pyrrolidinocarbonyl, piperidinocarbonyl, morpholinocarbonyl, thiomorpholinocarbonyl group and the piperazinocarbonyl or 4-methylpiperazinocarbonyl group, as well as a phenylcarbamoyl, diphenylcarbamoyl and benzylcarbamoyl group which is unsubstituted or substituted by lower alkyl, lower alkoxy, halogen and/or nitro.

The nitrogen atoms of the amidino and carbazoyl groups can also be substituted in like manner; however, the carbazoyl group is preferably substituted only at the terminal nitrogen atom. The particularly preferred amidino group is that wherein both nitrogen atoms are substituted by a phenyl radical. The carbamoyl and carbazoyl groups are preferably unsubstituted.

A hydrocarbon radical is an acyclic, carbocyclic, or carbocyclic-acyclic, heterocyclic or heterocyclic-acyclic hydrocarbon radical which contains preferably not more than 18 carbon atoms. A heterocyclic and heterocyclic-acyclic radical corresponds to a carbocyclic and carbocyclic-acyclic radical respectively, in which one, two or more ring carbon atoms are replaced by heteroatoms. Preferred heteroatoms are oxygen, sulphur and nitrogen atoms. These radicals can be unsubstituted or substituted and contain one, two, or more multiple bonds, such as double and triple bonds. Cyclic radicals, wherein at least one 6-membered carbocyclic ring or a 5- to 8-membered heterocyclic ring is completely unsaturated (i.e. containing the maximum number of non-cumulated double bonds) are designated as aromatic radicals. Carbocyclic radicals in which at least one ring is a 6-membered aromatic ring (i.e. the benzene ring) are designated as aryl radicals.

A monovalent acyclic hydrocarbon radical is in particular a linear or branched lower alkyl, lower alkenyl, lower alkadienyl or lower alkynyl radical. An acyclic ylidene radical is an analogous radical in which two free valencies originate from a single carbon atom and is in particular a lower alkylidene and lower alkenylidene radical.

Examples of lower alkyl radicals are methyl, ethyl, n-propyl, isopropyl, n-butyl, isobutyl, sec-butyl or tert-butyl, as well as n-pentyl, isopentyl, n-hexyl, isohexyl or n-heptyl. Examples of lower alkenyl radicals are: vinyl, allyl, propenyl, isopropenyl, 2- or 3-methallyl and 2- or 3-butenyl. Lower alkynyl is for example propargyl or 2-butynyl. Examples of lower alkylidene radicals are methylene, isopropylidene or isobutylidene, and a lower alkenylidene radical is for example vinylidene.

A monovalent carbocyclic hydrocarbon radical is in particular a monocyclic cycloalkyl radical or a mono- or bicyclic aryl radical. Radicals containing not more than 12 ring carbon atoms and 5- and/or 6membered rings are preferred. Such radicals can also carry one or more lower alkyl radicals or further carbocyclic radicals. A carbocyclic ylidene radical is an analogous radical in which two free valencies originate from a single carbon atom and is in particular a monocyclic cycloalkylidene radical. Carbocyclic-acyclic radicals are hydrocarbon radicals in which an acyclic monovalent radical or an acyclic ylidene radical, in particular one containing not more than 7, preferably not more than 4, carbon atoms, carries one or more carbocyclic, optionally aromatic, radicals as defined above. Cycloalkyl-lower alkyl or aryl-lower alkyl and cycloalkyl-lower alkylidene or aryl-lower alkylidene radicals are to be particularly mentioned.

Examples of cycloalkyl radicals are cyclopropyl, cyclobutyl, cyclopentyl, cyclohexyl, cycloheptyl and cyclooctyl, and examples of cycloalkylidene radicals are cyclopentylidene or cyclohexylidene. Cycloalkyl-lower alkyl radicals are for example cyclopropylmethyl, cyclopentylmethyl, cyclohexylmethyl or cycloheptylmethyl, 1- or 2-(cyclopropyl)ethyl, 1- or 2-(cyclopentyl)ethyl, 1- or 2-(cyclohexyl)ethyl and 1- or 2-(cycloheptyl)ethyl, and also dicyclohexylmethyl and tricyclohexylmethyl. A cycloalkyl-lower alkylidene radical is for example cyclohexylmethylene or dicyclomethylene.

An aryl radical is in particular a phenyl radical, and also a naphthyl radical, such as 1- or 2-naphthyl, a biphenylyl radical, as in particular 4-biphenylyl, as well as an anthryl, fluorenyl and azulenyl radical. Preferred aryl-lower alkyl and aryl-lower alkylidene radicals are for example phenyl-lower alkyl or phenyl-lower alkenyl radicals, for example benzyl, 1- or 2-phenylethyl, 1-, 2- or 3-phenylpropyl, diphenylmethyl (i.e. benzhydryl), trityl and 1- or 2-naphthylmethyl radicals, and benzylidene.

Heterocyclic radicals, in particular those of heterocyclic or heterocyclic-acyclic carboxylic acids, are in particular monocyclic aza-, thia-, oxa-, thiaza-, thiadiaza-, oxaza-, diaza-, triaza- or tetraazacyclic radicals, preferably of aromatic character, and can carry further acyclic, carbocyclic or heterocyclic radicals, and can be mono-, di-, or polysubstituted. The acyclic portion of heterocyclic-acyclic radicals preferably has the meaning as that for example of the corresponding portion of the carbocyclic-acyclic radicals.

The above hydrocarbon radicals, including heterocyclic radicals, can be substituted by one, two, or more identical or different substituents. Possible substituents or aromatic radicals are in particular: halogen atoms, such as chlorine and fluorine atoms, and also bromine and iodine atoms, nitro groups and lower alkoxy groups, for example methoxy, ethoxy, propoxy, 2-propoxy and tert-butoxy, and also methylenedioxy. A particularly preferred substituent of aliphatic, i.e. acyclic and saturated carbocyclic, hydrocarbon radicals, as well as of the acyclic portion of carbocyclic and heterocyclic-acyclic hydrocarbon radicals, is a hydroxyl group, in particular a hydroxyl group in the 1-position, or an oxo group. They can be in the free or else in a functionally modified form. The hydroxyl group can be for example in an esterified form, for example esterified with the acyl group $Ac^1$. In the free form the oxo group is an aldehydo or keto group, and in the functionalised form it is in particular an acetalised or ketalised oxo group or also an oximino or alkoximino group, for example the methoximino group. The acetal-forming or ketal-forming alcohol component is preferably a lower alkanol, such as methanol, ethanol, propanol or butanol, or in particular a lower alkanediol the hydroxyl groups of which are separated from one another by 3, or in particular 2, carbon atoms, for example 1,2-propanediol, 1,3-propanediol, 2,3-butanediol and especially 1,2-ethanediol. Such an oxo group can also form an inner hemiketal with the hydroxyl group in the 6-position of the bicyclomycin ring. A free oxo group is preferably in the 1-position of the acyclic portion of a hydrocarbon radical. Such a radical corresponds formally to the acyl radical of a carboxylic acid, for example one of those referred to hereinafter, and is in particular represented by the following particularly preferred radicals: formyl, acetyl, propionyl, butyryl, benzoyl, phenylacetyl, 1- or 2-phenylpropionyl, and also the corresponding radicals in which the phenyl ring is substituted in the manner indicated above.

The acyl group $Ac^1$ is the monovalent radical derived from a hemiderivative of carbonic acid, from a carboxylic acid or from formic acid, i.e. the formyl group, and an analogous radical which contains sulphur instead of oxygen. The acyl radical of a hemiderivative of carbonic acid is in particular the acyl radical of a corresponding hemiester, for example peferably a lower alkoxycarbonyl or aryl-lower alkoxycarbonyl group which is unsubstituted or substituted in particular by lower alkyl, lower alkoxy, nitro and/or halogen, such as methoxycarbonyl, ethoxycarbonyl, tert-butoxycarbonyl, 2,2,2-trichloroethoxycarbonyl, 2-iodoethoxycarbonyl, benzyloxycarbonyl, 2-phenyl-2-propoxycarbonyl, 2-p-tolyl-2-propoxycarbonyl, 2-p-biphenylyl-2-propoxycarbonyl, 1,1-diphenylethoxycarbonyl or p,p'-dimethoxybenzhydryloxycarbonyl group. An acyl group derived from a carboxylic acid is a group in which one of the above defined substituted or unsubstituted acyclic, carbocyclic, carbocyclic-acyclic, heterocyclic and heterocyclic-acyclic radicals is bonded to the carbonyl group. Acyl radicals of the following monocarboxylic acids having not more than 18 carbon atoms are particularly preferred: acyclic carboxylic acids, in particular lower alkanecarboxylic acids, such as propionic, butyric, isobutyric, baleric, isovaleric, capronic, trimethylacetic, enanthic and diethylacetic acid, and, most preferably, acetic acid, but also corresponding halogenated lower alkanecarboxylic acids, such as chloroacetic acid, bromoacetic acid or α-bromoisovaleric acid; carbocyclic or carbocyclic-acyclic monocarboxylic acids, for example cyclopropane-, cyclobutane-, cyclopentane- and cyclohexanecarboxylic acid and cyclopropyl-, cyclobutyl-, cyclopentyl- or cyclohexyl-acetic acid or cyclopentyl- or cyclohexylpropionic acid; aromatic carbocyclic acids, for example benzoic acids which are unsubstituted or substituted by halogen, such as fluorine, chlorine or bromine atoms, and/or by hydroxyl, lower alkoxy, lower alkyl and nitro groups; aryl- or aryloxy-lower alkanecarboxylic acids and the analogues thereof which are unsaturated in the chain, for example phenylacetic or phenoxyacetic acids which are unsubstituted or substituted by the same substituents as indicated above for benzoic acid, phenylpropionic acids and cinnamic acids; and also heterocyclic acids, for example furane-2-carboxylic acid, 5-tert-butylfurane-2-carboxylic acid, 5-bromofurane-2-carboxylic acid, thiophene-2-carboxylic acid, nicotinic or isonicotinic acid, 3-(4-pyridyl)-propionic acid, and pyrrol-2- or -3-carboxylic acids which can be substituted by lower alkyl groups, and corresponding α-aminoacids, in particular α-amino-lower alkanecarboxylic acids, for example glycine, phenylglycine, proline, leucine, valine, tyrosine, histidine and asparagine.

A bivalent acyl radical $Ac^2$ is derived chiefly from a dicarboxylic acid having not more than 18 carbon atoms which in turn is derived from the above optionally substituted acyclic, carbocyclic, carbocyclic-acyclic, heterocyclic and heterocyclic-acyclic radicals in that it carriers two carboxyl groups, optionally also at the heteroatoms. Examples of such dicarboxylic acids are: oxalic acid, malonic acid, mono- or di-lower alkylmalonic acid, succinic acid, glutaric acid, adipic acid, maleic acid, itaconic acid, citraconic acid, angelic acid, 1,1-cyclopentane- or 1,1-cyclohexane-dicarboxylic acid, a phthalic, quinolic or phenylsuccinic acid which is unsubstituted or substituted by halogen atoms, such as fluorine, chlorine or bromine atoms, and/or lower alkyl, lower alkoxy and nitro groups, and also tartronic acid, mesoxalic acid, oxalacetic acid, malic acid, tartaric acid, a tartaric acid which is esterified or etherified at the hydroxyl groups, glutamic acid and aspartic acid and derivatives of these last two acids with protected amino groups. $Ac^2$ can also be a divalent radical of ortho-carbonic acid or of an ortho-carboxylic acid, in particular a di-lower alkoxymethylene group, or a 1-lower alkoxyalkylidene or a α-lower alkoxybenzylidene group, for example methoxymethylene, 1-methoxyethylidene, ethoxymethylene, 1-ethoxyethylidene, α-methoxybenzylidene and α-ethoxybenzylidene group.

The compounds of the formula I can be in the form of salts, preferably of physiologically tolerable salts, if a free carboxyl group is present as substituent X and/or Y. Such salts are in particular metal or ammonium salts, such as alkali metal and alkaline earth metal salts, for example sodium, potassium, magnesium or calcium salts, and also ammonium salts with ammonia or suitable organic amines. Suitable amines as salt-forming components are in particular acyclic, carbocyclic and carbocyclic-acyclic primary, secondary and, most preferably, tertiary mono-, di- or polyamines, and heterocyclic bases, such as lower alkylamines, for example triethylamine, hydroxy-lower alkylamines, for example 2-hydroxyethylamine, di-(2-hydroxyethyl)-amine or tri-(2-hydroxyethyl)-amine, basic aliphatic esters of carboxylic acids, for example 2-(diethylamino)-ethyl 4-aminobenzoate, lower alkylenamines, for example 1-ethyl-piperidine, cycloalkylamines, for example dicyclohexylamine, or benzylamines, for example N,N'-dibenzylethylenediamine, and bases of the pyridine type, for example pyridine, collidine or quinoline. Preferred salt-forming components are those which result in physiologically tolerable salts.

The novel compounds of the present invention exhibit useful pharmacological, especially antibiotic, for example antibacterial, properties, and/or they can be used as intermediates for obtaining such compounds.

Particularly preferred compounds are those of the formula

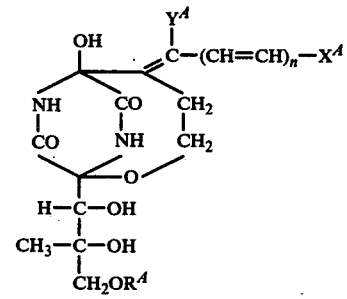

(IA)

wherein $X^4$ represents halogen, an unsubstituted or substituted phenyl radical Ph, a free or modified lower alkyl or lower alkenyl radical alk or, in particular, represents a free or functionally modified carboxyl group, Y represents hydrogen or has one of the meanings assigned to $X^4$, $R^4$ represents a monovalent acyl group $Ac^4$ or hydrogen, and n is 0 or 1, and salts of these compounds, provided they contain salt-forming groups.

Halogen can be bromine and iodine and, in particular, fluorine or chlorine.

The phenyl radical Ph can be substituted by one or more halogen atoms, such as fluorine, chlorine or bromine atoms, or by nitro groups, lower alkyl radicals, such as methyl and ethyl radicals, and/or by lower alkoxy groups, such as methoxy, ethoxy and also methylenedioxy groups.

The radical alk is in particular one of the unsubstituted, preferably linear, lower alkyl or lower alkenyl radicals referred to above, such as the methyl, ethyl, propyl, butyl, vinyl and allyl radical, which can be modified in that it carries one or more radicals Ph as defined above and/or is substituted by a free or functionally modified oxo group, in particular a free oxo group in the 1-position. Examples of such modified radicals alk are: benzyl, benzhydryl (=diphenylmethyl), trityl (=triphenylmethyl), 1- or 2-phenylethyl, 2-phenylpropyl and 4-phenylbutyl, and the corresponding radicals in which the aromatic portion is substituted in the above manner, such as p-nitrobenzyl, p-methylbenzyl, veratryl, 3,4,5-trimethoxybenzyl, 2-p-chlorophenylethyl and di-(p-methylphenyl)-methyl. Examples of substituted radicals alk are: formyl, acetyl, propinoyl, butyryl, pentanoyl and hexanoyl, and also benzoyl, p-nitrobenzoyl, p-chlorobenzoyl, p-methoxybenzoyl, veratroyl, m- and p-toluoyl, phenylacetyl, 2- and 3-phenylpropionyl, 3,3-diphenylpropionyl and 4-phenylbutyryl, as well as 1-hydroxyethyl. The functionally modified oxo group in the radicals alk is in particular an oxo group in the form of an oxime or O-alkyloxime, for example an O-lower alkyloxime, such as O-methyloxime, or an oxo group which is acetalised or ketalised by a lower alkanol, such as methanol and ethanol, or by an α- or β-alkanediol, such as 1,2-ethanediol (=ethylene glycol) or 1,3-propanediol. Correspondingly substituted radicals alk are in particular: oximinomethyl, 1-oximinoethyl and 1-methoxyiminoethyl or dimethoxymethyl, diethoxymethyl, 1,3-dioxolan-2-yl (=ethylenedioxymethyl), 1,3-dioxan-2-yl, (=trimethylenedioxymethyl), 2,2-dimethoxyethyl, 2,2-dimethoxypropyl, 3,3-dimethoxypropyl, 1,3-dioxolan-2-yl-methyl, 2-methyl-1,3-dioxolan-2-yl-methyl and 2-(1,3-dioxolan-2-yl)-ethyl, and also 2,2-dimethoxy-2-phenylethyl, 3,3-dimethoxy-3-phenyl-propyl, 2-phenyl-1,3-dioxolan-2-yl-methyl, 2-p-nitrophenyl-1,3-dioxolan-2-yl-methyl and 2-(2-phenyl-1,3-dioxolan-2-yl)-ethyl.

The definition of the expression "a functionally modified carboxyl group" has already been given when indicating the meaning of the symbol X.

The acyl radical $Ac^4$ is the monovalent radical of a hemiderivative of carbonic or thiocarbonic acid, for example the methoxycarbonyl, ethoxycarbonyl, tert-butoxycarbonyl or benzyloxycarbonyl group, and also the radical of a modified or unmodified lower alkanecarboxylic acid or of an unsubstituted or substituted monocyclic aryl- or heterocyclylcarboxylic acid, and also the formyl group. The modified or unmodified lower alkanecarboxylic acids can carry unsubstituted or substituted monocyclic aryl and/or heterocyclyl radicals and/or be substituted in the aliphatic portion by functional groups. Preferred substituents are halogen atoms, in particular chlorine or fluorine atoms, and also primary amino groups, tertiary amino groups, for example dimethylamino, diethylamino and piperidino, morpholino and N'-methylpiperazino groups and carboxyl groups which can be in the free form, as salts or as lower alkyl esters, in particular methyl and ethyl esters. The monocyclic aryl and heterocyclyl radicals which are present in the acyl radical $Ac^4$ are in particular phenyl, furyl, thienyl, pyridyl, pyrimidyl, oxazolyl, imidazolyl and tetrazolyl radicals, and they can be substituted in the same manner as indicated above in respect of the radical Ph. Examples of such modified or unmodified radicals of lower alkanecarboxylic acids are in particular: acetyl, propionyl, butyryl, methoxalyl, glycyl, N,N-dimethylglycyl, phenylacetyl, furylacetyl, p-nitrophenylacetyl, m- and p-chlorophenylacetyl, chloroacetyl, trichloroacetyl, and succinamoyl. Examples of unsubstituted or substituted monocyclic radicals of aryl- and heterocyclylcarboxylic acids are in particular: benzoyl, p-nitrobenzoyl, p-methoxybenzoyl, p-chlorobenzoyl, o-, m- and p-toluoyl, 2,4,6-trimethylbenzoyl, furoyl, thenoyl, 2-pyridinecarbonyl, nicotinoyl, isonicotinoyl, and 1- and 5-tetrazolcarbonyl.

As has already been mentioned above, the novel compounds, in particular those of the formula IA, are distinguished by their useful pharmacological properties, as for example results of in vitro tests demonstrate. Accordingly, they possess for example antibiotic, in particular antibacterial, properties, in that they inhibit the growth of microorganisms, such as Enterobacteriaceae (in concentrations of approx. 12.5 to approx. 100 mcg/ml) or *Proteus sp.* (in concentrations of approx. 25 to approx. 100mcg/ml), in the agar dilution test. Compared with bicyclomycin (cf. German Offenlegungsschrift 2,150,593), the novel compounds have furthermore the advantage that they are also active against *Proteus sp.*

Compounds to be singled out for special mention are those of the formula IA wherein n is O and $R^4$ is replaced by the symbol $R^B$, which represents a lower alkanoyl, phenyl-lower alkanoyl or benzoyl radical or in particular a hydrogen atom, and the aromatic rings of these radicals can be substituted by nitro, methoxy, methyl and/or halogen, in particular chlorine or fluorine. Examples of these particularly preferred radicals are: formyl, acetyl, propionyl, butyryl, phenylacetyl, p-chlorophenylacetyl, benzoyl, o-, m- and p-toluoyl, m- and p-chlorobenzoyl, p-nitrobenzoyl, p-methoxybenzoyl and 3,4-dimethoxybenzoyl.

Among these compounds, particularly preferred compounds are those of the formula

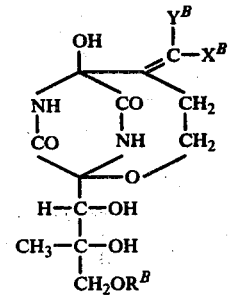 (IB)

wherein $R^B$ has the above meaning, $X^B$ represents the cyano group or a group of the formula —C(=O)Z, $Y^B$ has one of the meanings assigned to $X^B$ or represents hydrogen or chlorine, and Z represents a hydrogen atom, a hydroxyl, amino or hydrazino group, a phenyl radical or a lower alkyl or lower alkoxy radical which can be modified by phenyl, and the aromatic rings of all these radicals can be substituted by nitro, methoxy, methyl and/or halogen, in particular chlorine or fluorine, and pharmacologically useful salts of compounds in which Z represents hydrogen.

The most preferred compounds are those of the formula IB, wherein RB represents a hydrogen atom, $X^B$ represents the cyano, carboxyl or $C_1$–$C_4$-lower alkoxycarbonyl group and $Y^B$ represents hydrogen or has one of the preferred meanings of $X^B$, and pharmacologically useful salts of the compounds which contain free carboxyl groups. Among these compounds, mention is to be made for example of bicyclomycin-5a-carboxylic acid and the nitrile and, in particular, the methyl and ethyl ester thereof, and also the sodium and potassium salt thereof.

The novel compounds can therefore be used for example in the form of antibiotic preparations for the treatment of infectious diseases, or as disinfectants or preservatives, or as additives to animal feeds. In addition, they can be used as intermediates for obtaining such compounds with antibiotic action.

The compounds of the formula I are obtained by reacting a 5-norbicyclomycin-5-one compound of the formula II

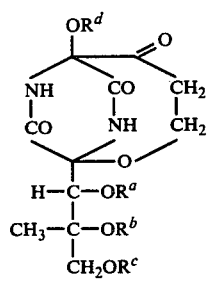

wherein $R^1$, $R^b$, $R^c$ and $R^d$ are as defined in formula (I), with a compound of the formula

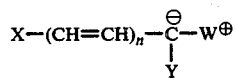

wherein X, Y and n have the indicated meanings and $W^\oplus$ represents a trisubstituted phosphonio group or a diesterified phosphono group together with a cation, and, if desired, in a resultant compound, removing or introducing one or more hydroxyl protective groups $R^a$, $R^b$, $R^c$ and/or $R^d$ or converting them into other hydroxyl protective groups, and/or setting free functionally modified carbonyl or carboxyl groups or converting them into other functionally modified carbonyl or carboxyl groups, or functionally modifying free carbonyl or carboxyl groups, and/or, if desired, converting a resultant compound with a salt-forming group into a salt or a resultant salt into the free compound or into another salt, and/or, if desired, separating individual isomers from a resultant isomer mixture.

Starting materials of the formula II can contain both free and protected hydroxyl groups. However, a special temporary protection of free hydroxyl groups during the reaction of the present invention is not necessary in every case.

Starting materials of the formula III with a reactive phosphorus-containing functional group are designated as Wittig reagents. The group $W^\oplus$ in the starting material of the formula (III) is a phosphonio or phosphono group which is ordinarily used in Wittig condensation reactions, in particular a triarylphosphonio, for example a triphenylphosphonio group, or tri-lower alkylphosphonio, for example tributylphosphonio group, or a phosphono group which is diesterified by lower alkyl, for example ethyl, and the symbol $W^\oplus$, if it represents the phosphono group, additionally comprises the cation of a strong base, in particular a suitable metal ion, such as an alkali metal ion, for example a lithium, sodium or potassium ion. The group $W^\oplus$ is preferably on the one hand a triphenylphosphonio and tributylphosphonio group, and on the other, a diethylphosphono group together with an alkali metal ion, for example a sodium ion.

In phosphonium compounds of the formula (III), which in the isomeric ylene form are also designated as phosphorane compounds, the negative charge is neutralised by the positively charged phosphonium group. In phosphono compounds of the formula (III), which in their isomeric form can also be designated as phosphonate compounds, the negative charge is neutralised by the cation of a strong base which, depending on the method of preparing the phosphono starting material, can be for example an alkali metal ion, for example a sodium, lithium or potassium ion. The phosphonate starting materials are therefore used as salts in the reaction.

The actual reactive form is illustrated by formula (III), in which the reagent acts on the ketone component of the formula (II). The starting material employed is however normally characterised by the alternative equivalent formula

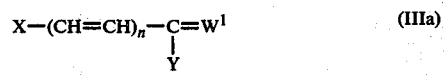

wherein X, Y and n have the above meanings and $W^1$ represents a trisubstituted radical, in particular a triaryl-, for example triphenylphosphoranylidene, radical, or a tri-lower alkyl-, for example tri-n-butyl-phosphoranylidene radical, or, if the starting material is a phosphono compound, by the formula

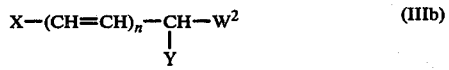

wherein X, Y and n have the indicated meanings and $W^2$ represents a phosphono group, in particular a dialkylphosphono, for example diethylphosphono, group. It will be understood however that a phosphono starting material of the formula (IIIb) is used in the form of a salt through being converted into the salt form illustrated by formula (III) suitable for the condensation by treatment with a suitable basic reagent, such as an inorganic base, for example an alkali metal carbonate, for example sodium or potassium carbonate, or an organic base, such as a tri-lower alkylamine, for example triethylamine, or a cyclic base of the amidine type, such as a corresponding diazabicycloalkene compound, for example 1,5-diaza-bicyclo[5.4.0]undec-5-ene.

If the Wittig reagent of the formula III contains functional groups, such as carbonyl or carboxyl groups, it is — with few exceptions — advantageous if these groups are in a protected form. Carbonyl groups are preferably protected by ketalisation or acetalisation, preferred alcohol components being the lower alkanols and lower alkanediols referred to above. The exception is a radical X wherein the carbonyl group is in the 1-position, in which case the carbonyl group preferably remains free. Normally, compounds of the formula (III) contain no free carboxyl groups, the sole exception being phosphono compounds of the formula (IIIb) wherein X or Y represents a free carboxyl group in the form of a metal salt, preferably alkali metal salt, such as a lithium, sodium or potassium salt. If it is desired to obtain a final product of the formula (I), wherein X and/or Y represents a free carboxyl group, preferably a starting material of the formula (III) is used, wherein the carboxyl group forms an esterified carboxyl group with a group $Z^x$ which can readily be replaced by hydrogen, especially under mild conditions. Such a group is in particular an α-polybranched lower alkyl group, for example a tert-butyl group, a lower alkenyl group, in particular a 2-lower alkenyl group, for example an allyl group, or a 2-halogeno-lower alkyl group, for example a 2,2,2-trichloroethyl, 2-bromoethyl or 2-iodoethyl group; a 2-lower alkylsulphonyl-lower alkyl group, for example a 2-methylsulphonylethyl group, or a 1-phenyl-lower alkyl group which is unsubstituted or substituted by lower alkoxy (for example methoxy) or by nitro, such as a benzyl or diphenylmethyl group which is unsubstituted or substituted as indicated, for example the benzyl, 4-methoxybenzyl, 4-nitrobenzyl, diphenylmethyl or 4,4'-dimethoxy-diphenylmethyl group; and also an organic silyl group, such as a tri-lower alkylsilyl, for example trimethylsilyl, group. These groups $Z^x$ are particularly suitable for being split off after the Wittig reaction. The splitting-off is performed in a manner known per se and is accompanied by liberation of the carboxyl group.

The process of the present invention is carried out in a manner which is known per se, preferably in the presence of a suitable inert solvent, for example in an aliphatic, cycloaliphatic or aromatic hydrocarbon, for example hexane, cyclohexane, benzene or toluene, a halogenated hydrocarbon, for example methylene chloride, an ether, for example diethyl ether, a lower alkylene glycol di-lower alkyl ether, for example dimethoxyethane or diethylene glycol dimethyl ether, a cyclic ether, for example dioxane or tetrahydrofurane, a carboxamide, for example dimethyl formamide, a di-lower alkyl sulphoxide, for example dimethyl sulphoxide, or a lower alkanol, for example methanol, ethanol or tert-butanol, or in a mixture thereof, and, if necessary, in an inert gas atmosphere, for example in an atmosphere of argon or nitrogen, and preferably in the absence of water. The reaction can take place at room temperature, but in most cases it is assisted advantageously by heating, for example in the temperature range between 30° and 120° C., preferably between approx. 50° and approx. 100° C.

Protected hydroxyl groups in the final products of the formula (I), for example the hydroxyl groups protected by etherification or esterification, preferably those which are protected by the protective groups represented by $R^1$, $R^2$ and $R^3$, can, if desired, be set free in a manner known per se individually or together. Accordingly, for example, hydroxyl groups which are protected as tetrahydropyranyl ether, such as those in the 1',3'- and/or 6-position, or as acetonide, such as those in the 2',3'-position, can be set free by conventional acid catalysed hydrolysis.

However, in final products of the formula (I) which contain at least one hydroxyl group, for example in which at least one of the symbols $R^a$, $R^b$, $R^c$ and $R^d$ represents hydrogen, the hydroxyl group can be esterified by methods which are known per se, in particular by treatment with acids, such as carboxylic acids, or with reactive derivatives thereof, such as anhydrides, halides, for example chlorides, and ketenes.

A ketalised or acetalised oxo group present in a compound of the formula (I) can be converted in a manner which is known per se into the free oxo group, for example by conventional acid catalysed hydrolysis.

A free oxo group present in an final product of the formula I can be converted into a functionalised oxo group, for example into the corresponding oxime in a manner known per se by treatment with hydroxylamine or with an O-substituted, such as O-lower alkylated, hydroxylamine, or with an acid addition salt of these compounds. If such an oxo group is at a suitable distance from the free hydroxyl group in the 6-position, as is the case for example of a carbonyl group which is bonded to the 5a-carbon atom, then both groups can combine to form a cyclic hemiketal (cf. Example 16). A free oxo group can also be functionally modified in such a manner that it is reduced in a manner known per se to form a corresponding hydroxyl group. For this purpose, diborane or complex metal hydrides, in particular boron hydrides, such as potassium or especially sodium borohydride, are used.

In a final product of the formula (I), wherein a carboxyl group together with a group $Z^x$ which can be easily replaced by hydrogen forms an esterified carboxyl group, this latter can be converted into the free carboxyl group in a manner known per se, for example depending on the nature of the group $Z^x$. Accordingly, a carboxyl group which is esterified by a suitable 2-halolower alkyl, arylcarbonylmethyl or 4-nitrobenzyl group can be converted into the free carboxyl group by treatment with a reducing agent, such as a metal, for example zinc, or with a reducing metal salt, such as a chromium(II) salt, for example chromium(II) chloride, usually in the presence of a hydrogen donor which, together with the metal, is able to produce nascent hydrogen, such as of an acid, in particular acetic acid, and also formic acid, or of an alcohol, preferably with the addition of water. Starting from a suitably esterified form, the carboxyl group can also be set free as follows:

a carboxyl group which is esterified by an arylcarbonylmethyl group: by treatment with a nucleophilic, preferably salt-forming reagent, such as sodium thiophenolate or sodium iodide, a carboxyl group which is esterified by 4-nitrobenzyl: by treatment with an alkali metal dithionite, for example sodium dithionite, a carboxyl group which is esterified by a 2-lower alkylsulphonyl-lower alkyl group: by treatment with a base, a carboxyl group which is esterified by a suitable arylmethyl group: by irradiation with ultraviolet light, for example at wavelengths under 290 mµ if the arylmethyl group represents a benzyl radical which can be substituted in the 3-, 4- and/or 5-position, for example by lower alkoxy and/or nitro groups, or with wavelengths above 290 mµ if for example the arylmethyl group represents a benzyl radical which is substituted in the 2-position by a nitro group, a carboxyl group which is esterified by a suitably substituted methyl radical, such as tert-butyl or diphenylmethyl: by treatment with a suitable acid agent, such as formic acid or trifluoroacetic acid, optionally with the addition of a nucleophilic compound, such as phenol or anisol, an esterified carboxyl group which can be split by hydrogenolysis, for example a benzyloxycarbonyl or 4-nitrobenzyloxycarbonyl group: by hydrogenolysis, for example by treatment with hydrogen in the presence of a noble metal catalyst, for example a palladium catalyst. A carboxyl group which is esterified by a lower alkenyl radical, for example by 2-lower alkenyl, in particular allyl, can be converted into the formylmethoxycarbonyl group by oxidation, for example by treatment with ozone, followed by a reducing agent, such as an agent which forms the epoxy group, for example dimethyl sulphide; from this formylmethoxycarbonyl group the carboxyl group can be set free by treatment with a base, such as a secondary amine, for example dimethylamine: Alternatively, a 2-lower alkenyloxycarbonyl group, for example allyloxycarbonyl, can be isomerised inter alia by treatment with tris-triphenylphosphinerhodium chloride, palladium on carbon, or with an alkali metal lower alkanolate, for example potassium tert-butylate, in dimethyl sulphoxide, to give a 1-lower alkenyloxycarbonyl group which is split by hydrolysis under weakly acid or weakly basic conditions. A carboxyl group which is protected by silylation can be set free in the conventional manner by solvolysis, for example by treatment with water or an alcohol.

In resultant final products of the formula (I), free or functionally modified carboxyl groups can be converted into other functionally modified carboxyl groups in a manner which is known per se.

Accordingly, for example, it is possible to esterify a free carboxyl group. Esterification is effected for example by treating the free acid with a suitable diazo compound, such as a diazo-lower alkane, for example diazomethane or diazobutane, or with a phenyldiazo-lower alkane, for example diphenyldiazomethane, if necessary in the presence of a Lewis acid, for example boron trifluoride. The esterification is also carried out by reaction with an alcohol in the presence of an esterifying agent, such as a carbodiimide, for example dicyclohexylcarbodiimide, or carbonyldiimidazole, as well as with a N,N'-disubstituted O- or S-substituted isourea or isothiourea in which the O- or S-substituent is for example lower alkyl, in particular tert-butyl, phenyl-lower alkyl or cycloalkyl, and the N- and/or N'-substituents are for example lower alkyl, in particular isopropyl, cycloalkyl or phenyl radicals. Known and suitable esterification methods include for example the conversion of the free carboxyl group into a salt and the reaction of the salt with a reactive ester of an alcohol and a strong mineral acid or organic sulphonic acid, as well as the primary formation of the acid halides, for example chlorides (prepared for example by treatment with oxalyl chloride), of activated esters (formed for example with a N-hydroxysuccinimide) or of mixed anhydrides (obtained for example with lower alkyl esters of haloformic acid, such as ethyl chloroformate or isobutyl chloroformate, or with haloacetic halides, such as trichloroacetyl chloride) and reaction of these reactive intermediates with alcohols, optionally in the presence of a base, such as pyridine.

These reactive intermediates can also advantageously be used as intermediate steps for the conversion of a free carboxyl group into a carbamoyl or carbazoyl group the nitrogen atoms of which can be substituted, for example in particular by lower alkyl radicals, in which case such a reactive compound is treated with ammonia or hydrazine hydrate, or with a N-substituted, in particular N-lower alkylated, derivative thereof, in a manner which is known per se. Carboxyl groups which are present in the final products of the formula (I) can also be converted with the same nitrogen-containing reagents into the corresponding carbamoyl and carbazoyl groups.

Salts of the compounds of the formula I can be prepared in a manner known per se. Thus salts of compounds of the formula I with a free carboxyl group can be formed for example by treatment with metal compounds, such as hydroxides, carbonates and hydrocarbonates of alkali metals or alkali metal salts of suitable carboxylic acids, for example with the sodium salt of α-ethylcaproic acid, or with ammonia or a suitable organic amine, preferably using stoichiometric amounts or only a small excess of the salt-forming agent.

Salts can be converted in the customary manner into the free compounds, metal and ammonium salts for example by treatment with suitable acids.

Resultant mixtures of stereoisomers can be separated into the individual isomers by methods which are known per se, for example by fractional crystallisation, adsorption chromatography (column or thin-layer chromatography), or other appropriate methods of separation.

The process also comprises those embodiments of the invention in which compounds obtained as intermediates are used as starting materials and the remaining process steps are carried out therewith or in which the process is interrupted at any stage, or in which starting materials can be used in the form of derivatives or formed during the reaction.

Preferably, the starting materials and reaction conditions are so chosen that the compounds referred to at the outset as being especially preferred are obtained.

The starting materials of the formula II used in accordance with the invention can be obtained by the oxidative elimination of the methylene group, for example by ozonisation, of the bicyclomycin or of a derivative thereof with protected hydroxyl groups, as described in Swiss Patent Application No. 6445/76 filed May 21, 1976 (Case 4-10487).

Compounds of the formula (IIIa) and (IIIb) are known or they can be obtained by methods which are known per se.

The pharmacologically useful compounds of the present invention can be used for example for obtaining pharmaceutical preparations which contain an effective amount of the active substance together or in admixture with inorganic or organic solid or liquid pharmaceutically useful carriers, which are suitable preferably for enteral, such as oral, or parenteral, administration.

Tablets or gelatin capsules are therefore used which contain the active substance together with diluents, for example lactose, dextrose, saccharose, mannitol, sorbitol, cellulose and/or glycin, and lubricants, for example silica, talc, stearic acid or salts thereof, such as magnesium or calcium stearate, and/or polyethylene glycol. Tablets also contain binding agents, for example magnesium aluminium silicate, starches, such as maize, wheat, rice or arrow root starch, gelatin, tragacanth, methyl cellulose, sodium carboxymethyl cellulose and/or polyvinylpyrrolidone, and, if desired, disintegrators, for example starches, agar, alginic acid or a salt thereof, such as sodium alginate, and/or effervescent mixtures, or adsorption agents, colourants, flavouring matters and sweeteners. Preferably the pharmacologically active compounds of the present invention are used in the form of preparations which can be administered by injection, for example, by intravenous injection, or of infusion solutions. Such solutions are preferably isotonic aqueous solutions or suspensions which can be prepared before use, for example from lyophilised preparations that contain the active substance alone or together with a carrier, for example mannitol.

The pharmaceutical preparations, can be sterilised and/or contain adjuvants, for example preservatives, stabilisers, wetting agents and/or emulsifiers, solubilisers, salts for regulating the osmotic pressure and/or buffers. The pharmaceutical preparations which, if desired, can contain further pharmacologically useful substances, are manufactured in known manner, for example using conventional mixing, granulating, confectioning, dissolving or lyophilising methods, and they contain from about 0.1% to 100%, especially from about 1% to about 50%, and lyophilisates up to 100% of the active substance. In particular, pharmaceutical preparations are prepared as dosage units.

The following non-limitative Examples will serve to illustrate the invention.

Preparation of the Starting Materials

A. A flow of ozone-enriched oxygen is introduced at −70° C. at a speed of approx. 20 liters/hr into a solution of 8 g of bicyclomycin monohydrate in 350 ml of methanol. After about 45 minutes, when a permanent blue colouration ensues, 2.2 ml of dimethyl sulphide are added and the reaction mixture is brought gradually to 0° C. The crystallised product is collected with suction and the mother liquor is concentrated to about a third of its volume and allowed to stand in order to obtain the second crop of crystals of the same quality. The resultant 5-nor-bicyclomycin-5-one has a melting point of 160°–162° C., which rises to 171°–175° C. after crystallisation from ethyl acetate-methanol.

B. A solution of 11.5 g of bicyclomycin-6,1′,3′-tri-tetrahydropyranyl ether in 200 ml of methanol is ozonised as described in A and treated with dimethyl sulphide. After it has warmed to room temperature, the reaction mixture is concentrated and the residue dissolved in a very small amount of ether. The solution is added dropwise into petroleum ether and the white amorphous precipitate is collected with suction and dried in a high vacuum. The resultant 5-nor-bicyclomycin-5-one-6,1′,3′-tri-tetrahydropyranyl ether melts unsharp between 65° to 75° C.

C. 3 g of bicyclomycin-3′-benzoate in methanolic solution are ozonised under the conditions of A. The excess ozone is destroyed with dimethyl sulphide and the solution is concentrated in a water jet vacuum. The residue is precipitated from methanol with ethyl acetate and yields amorphous 5-nor-bicyclomycin-5-one-3′-benzoate with a melting point of 125°–130° C.

D. A solution of 36 g of 5-norbicyclomycin-5-one in 600 ml of acetone and 1200 ml of dioxane is stirred with 360 ml of 2,2-dimethoxypropane (acetone dimethylketal) and 0.6 g of p-toluenesulphonic acid is added. The reaction mixture is stirred for 20 hours at room temperature, treated with 3.5 ml of triethylamine and concentrated in a water jet vacuum. The residue is dissolved in ethyl acetate and precipitated by addition of ether, affording 5-norbicyclomycin-5-one-2′,3′-acetonide with a melting point of 193°–195° C.

EXAMPLE 1

A mixture of 18.2 g of 5-nor-bicyclomycin-5-one in 60 ml of dioxane is treated with 20 g of methoxycarbonylmethylene-triphenylphosphorane and heated for 2 hours to 70° C. with stirring. The solvent is distilled off in a water jet vacuum and the residue is chromatographed through 200 g of silica gel Elution with a 4:1 mixture (v/v) of chloroform/methanol yields a product which, after crystallisation from water, gives 5a-methoxycarbonylbicyclomycin with a melting point of 135°–136° C.

EXAMPLE 2

Following the procedure of Example 1, a mixture of 1.82 g of 5-norbicyclomycin-5-one, 1.80 g of cyanomethylene-triphenylphosphorane and 60 ml of dioxane is stirred at 70° C. for 1 hour and worked up. On chromatography through 100 g of silica gel, elution with a 4:1 mixture (v/v) of chloroform/methanol yields a crude product which is recrystallised from acetonitrile to give a 5a-cyanobidyclomycin with a melting point of 180° C. (with decomp.).

EXAMPLE 3

Following the procedure of Example 1, a mixture of 3.04 g of 5-norbicyclomycin-5-one, 3.48 g of ethoxycarbonylmethylene-triphenylphosphorane and 100 ml of dioxane is stirred for 2¼ hours at 70° C. and worked up. On chromatography through 180 g of silica gel, elution with a 4:1 mixture (v/v) of chloroform/methanol yields a crude product which is recrystallised from water to give 5a-ethoxycarbonylbicyclomycin with a melting point of 128°–130° C.

EXAMPLE 4

Following the procedure of Example 1, a mixture of 3.04 g of 5-norbicyclomycin-5-one, 4.55 g of 4-nitrobenzyloxycarbonylmethylene-triphenylphosphorane and 100 ml of dioxane is stirred for 5 hours at 70° C. and worked up. On chromatography through 200 g of silica gel, elution with a 4:1 mixture (v/v) of chloroform/methanol yields a crude product which is crystallised from ethyl acetate to give 5a-(4-nitrobenzyloxycarbonyl)-bicyclomycin with a melting point of 165°–169° C.

EXAMPLE 5

A mixture of 2.4 g of 5a-(4-nitrobenzyloxycarbonyl)-bicyclomycin and 0.12 g of 10% palladium on charcoal in 100 ml of ethanol is hydrogenated at room temperature and slightly raised (by a few mm/Hg) pressure for 24 hours, in the course of which 473 ml of hydrogen is taken up. The catalyst is removed by filtration, the solution concentrated in a water jet vacuum and the residue is chromatographed through 40 g of silica gel. Elution with a 4:1 mixture (v/v) of chloroform/methanol yields 5a-carboxybicyclomycin in amorphous form.

EXAMPLE 6

A mixture of 6.5 g of 5-nor-bicyclomycin-5-one-6,1′,3′-tritetrahydropyranyl ether and 4.06 g of ethoxycarbonylmethylene-triphenylphosphorane in 175 ml of benzene is stirred for 5 hours at 70° C. The solution is concentrated and the residue is chromatographed through 200 g of silica gel. Elution with a 95:5 mixture (v/v) of chloroform/methanol yields crude 5a-ethoxycarbonylbicyclomycin-6,1′,3′-tri-tetrahydropyranyl ether. This ether is dissolved in 50 ml of methanol and the solution is treated with 20 ml of 50% (v/v) aqueous acetic acid. The mixture is stirred for 15 hours at 50° C. and concentrated in a water jet vacuum and the residue is chromatographed through 120 g of silica gel. Elution with a 4:1 mixture (v/v) mixture of chloroform/methanol yields a crude product which melts at 128°–130°

C. after recrystallisation from water and is identical with the 5a-ethoxycarbonylbicyclomycin of Example 3.

EXAMPLE 7

A mixture of 2.4 g of 5-nor-bicyclomycin-5-one-3'-benzoate in 100 ml of dioxane is treated with 2.08 g of carbamoylmethylene-triphenylphosphorane and heated with stirring for 2 hours to 50° C. The solvent is distilled off in a water jet vacuum and the residue is chromatographed through 200 g of silica gel. Elution with a 4:1 mixture (v/v) of chloroform/methanol yields a product which is crystallised from methanol to give 5a-carbamoylbicyclomycin-3'-benzoate melting over 200° C. (with decomp.).

EXAMPLE 8

A mixture of 6.88 g of 5-nor-bicyclomycin-5-one-2',3'-acetonide in 150 ml of dioxane is treated with 9.6 g of carbamoylmethylene-triphenylphosphorane and stirred for 1 hour to 50° C. The solvent is distilled off in a water jet vacuum and the residue is chromatographed through 250 g of silica gel. Elution with a 4:1 mixture (v/v) of chloroform/methanol yields a product which is crystallised from acetone to give 5a-carbamoylbicyclomycin-2',3'-acetonide melting over 185° C. (with decomp.).

EXAMPLE 9

A mixture of 1.36 g of 5a-carbamoylbicyclomycin-2',3'-acetonide in 100 ml of methanol and 1.72 ml of 2N sulphuric acid is stirred for 4 hours at room temperature, neutralised with solid barium hydroxide (octahydrate), freed from precipitated barium sulphate by filtration and concentrated in vacuo. The residue is washed with methanol, affording 5a-carbamoylbicyclomycin with a melting point of 204°-207° C.

EXAMPLE 10

Following the procedure described in Example 8, a mixture of 10.3 g of 5-nor-bicyclomycin-5-one-2',3'-acetonide, 9.9 g of cyanomethylene-triphenylphosphorane and 300 ml of dioxane is stirred for 7 hours at 60° C. and worked up. On chromatography through 500 g of silica gel, elution with a 9:1 mixture (v/v) of chloroform/methanol yields a crude product which is recrystallised from ethyl acetate to give 5a-cyanobicyclomycin-2',3'-acetonide with a melting point of 194°-195° C. (with decomp.).

EXAMPLE 11

Following the procedure described in Example 8, a mixture of 3.44 g of 5-nor-bicyclomycin-2',3'-acetonide, 5.31 g of 4-nitrobenzyloxycarbonylmethylene-triphenylphosphorane and 100 ml of dioxane is stirred for 7 hours at 70° C. and worked up. On chromatography through 300 g os silica gel, elution with a 4:1 mixture (v/v) of chloroform/methanol yields a crude product which is crystallised from ethyl acetate/ether to give 5a-(4-nitrobenzyloxycarbonyl)-bicyclomycin-2',3'-acetonide with a melting point of 126°-128° C.

EXAMPLE 12

A solution of 2.5 g of 5-nor-bicyclomycin-5-one in 30 ml of dioxane is treated at room temperature with 2.8 g of phenacylidene-tributylphosphorane and 0.95 g of 97% potassium tert-butylate and stirred for 24 hours at room temperature, filtered, and concentrated under reduced pressure. The oily residue is chromatographed through 400 g of silica gel. Elution with a 5:1 mixture (v/v) of chloroform/methanol and a 4:1 mixture (v/v) of ethyl acetate/methanol yields a product which is recrystallized from ethanol/pentane to give 5a-benzoyl-bicyclomycin with a melting point of 136°-146° C.

EXAMPLE 13

A mixture of 18.1 g of 5-norbicyclomycin-5-one in 400 ml of dioxane is treated with 22.1 g of acetonyltributylphosphonium chloride and 6.72 g potassium tert-butylate. The reaction mixture is then stirred for 6 hours at room temperature, filtered, and concentrated in a water jet vacuum. Initially, the residue is preliminarily purified through 600 g of silica gel with a 4:1 mixture (v/v) of ethyl acetate/ethanol and then chromatographed once more through 700 g of silica gel with 4:1 mixture (v/v) of chloroform/methanol, yielding a product which, after precipitation from methanolic solution with ethyl acetate, gives the amorphous 5a-acetylbicyclomycin with a melting point of 111°-119° C. Repetition of the same procedure starting from an equivalent amount of 5-norbicyclomycin-5-one-2',3'-acetonide yields 5a-acetylbicyclomycin-2',3'-acetonide which, after precipitation from a solution in ethyl acetate with ether, melts at 193°-195°.

EXAMPLE 14

A mixture of 3.8 g of 5a-acetylbicyclomycin, 1 g of O-methylhydroxylamine hydrochloride, 100 ml of ethanol and 1.8 ml of pyridine is stirred for 2½ hours at 50° C. and concentrated in a water jet vacuum. The residue is chromatographed through 100 g of silica gel; elution with a 4:1 mixture (v/v) of chloroform/methanol, yields a product which is recrystallised from ethyl acetate to yield 5a-(1-methoxyiminoethyl)-bicyclomycin with a melting point of 112°-116° C.

EXAMPLE 15

A solution of 2.2 g of 5a-acetylbicyclomycin in 50 ml of methanol is treated at 0° to 5° C. with 0.240 g of sodium borohydride in 2 portions, stirred for 1 hour at 0° to 5° C. and subsequently concentrated in a water jet vacuum. The residue is chromatographed through 20 g of silica gel; elution with a 2:1 mixture (v/v) of chloroform/methanol, yields a product which is recrystallised from methanol/ethyl acetate to yield 5a-(1-hydroxyethyl)-bicyclomycin (a mixture of both epimers at the newly formed hydroxyl group) with a melting point of 175°-182° C.

Repetition of this procedure starting from an equivalent amount of 5a-acetylbicyclomycin-2',3'-acetonide affords 5a-(1-hydroxyethyl)-bicyclomycin-2',3'-acetonide (a mixture of both epimers at the newly formed hydroxyl group) with a melting point of 114°-119° C. (amorphous).

EXAMPLE 16

A mixture of 1.3 g of 5a-acetylbicyclomycin, 0.247 g of sodium cyanoborohydride and 0.266 g of methylamine hydrochloride in 50 ml of dioxane is stirred overnight at room temperature, concentrated and poured onto a column of 75 g of silica gel. Elution with a 2:1 mixture of chloroform/methanol yields the amorphous inner hemiacetal of the starting compound of the formula

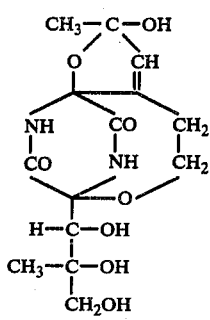

which melts at 123°–130° C. after precipitation with ethyl acetate from a methanolic solution.

EXAMPLE 17

A total amount of 3.6 ml of benzoyl chloride is added at 0° C. to a solution of 7.5 g of 5a-methoxycarbonylbicyclomycin in 45 ml of pyridine and the reaction mixture is thereafter stirred for 6 hours at room temperature. Water is then added dropwise to the reaction mixture and the solution is concentrated under reduced pressure. The residue is partitioned between ethyl acetate and water, the organic phase is washed neutral with water, dried over magnesium sulphate and concentrated once more. The residue is chromatographed through a column of 500 g of silica gel; elution with a 9:1 mixture (v/v) of chloroform/methanol, yields a product which is reprecipitated from ethyl acetate/pentane to give 5a-methoxycarbonylbicyclomycin-3'-benzoate with a melting point of 125°–133° C.

5a-Methoxycarbonylbicyclomycin-1',3'-dibenzoate with a melting point of 132°–144° C. is obtained as by-product from another fraction of the above described chromatography after reprecipitation from chloroform/pentane.

EXAMPLE 18

A mixture of 1.9 ml of isobutyl chloroformate and 20 ml of tetrahydrofurane is added dropwise over the course of 30 minutes to a vigorously stirred solution of 1.9 g of 5a-methoxycarbonylbicyclomycin in 40 ml of pyridine with cooling to −15° C. The mixture is then stirred for 1 hour at −10° C., filtered to remove precipitated pyridine hydrochloride, and concentrated in a high vacuum. Chromatography of the residue through silica gel with a 19:1 mixture (v/v) of chloroform/methanol yields two components: the more rapidly eluted 5a-methoxybicyclomycin-1',3'-O-dicarbonate and the more slowly eluted amorphous 3'-O-isobutyloxycarbonyl-5a-methoxycarbonylbicyclomycin; $[\alpha]_D = +34°$ ±1 (C=0.877; dimethylsulphoxide).

Example 19

A mixture of 2.5 ml of isopropyl chloroformate and 20 ml of tetrahydrofurane is added dropwise over the course of 20 minutes to a vigorously stirred solution of 2 g of 5a-methoxycarbonylbicyclomycin in 30 ml of pyridine with cooling to −15° C. The mixture is then stirred for 1 hour at +10° C., filtered to remove precipitated pyridine hydrochloride, and concentrated in a high vacuum. Chromatography of the residue through silica gel with a 19:1 mixture (v/v) of chloroform/methanol yields two components: the more rapidly eluted 5a-methoxycarbonylbicyclomycin-1',3'-O-dicarbonate and the more slowly eluted amorphous 3'-O-isopropoxycarbonyl-5a-methoxycarbonylbicyclomycin; $[\alpha]_D = +56° ± 1$ (C=1.031; dimethyl sulphoxide).

Example 20

A mixture of 3 ml of cyclohexyl chloroformate and 20 ml of tetrahydrofurane is added dropwise over the course of 20 minutes to a vigorously stirred solution of 2 g of 5a-methoxycarbonylbicyclomycin in 20 ml of pyridine with cooling to −15° C. The mixture is thereafter stirred for 1 hour at 0° C., filtered to remove precipitated pyridine hydrochloride, and concentrated in a high vacuum. Chromatography of the residue through silica gel with a 19:1 mixture (v/v) of chloroform/methanol yields 2 components: the more rapidly eluted 5a-methoxycarbonylbicyclomycin-1',3'-O-dicarbonate and the more slowly eluted amorphous 3'-O-cyclohexyloxycarbonyl-5a-methoxycarbonylbicyclomycin; $[\alpha]_D = +34° ±$ (C=1.033; dimethyl sulphoxide).

What is claimed is:

1. A 2-Oxa-7,9-diazabicyclo[4,2,2]decane of the formula

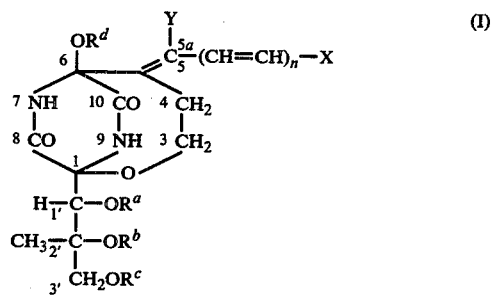

wherein each of $R^a$, $R^b$, $R^c$ and $R^d$ individually represents hydrogen, 2-oxaalkyl, 2-oxacycloalkyl or a monovalent acyl $Ac^1$ derived from formic acid, a lower alkyl hemiester of carbonic acid or from an acyclic or aromatic carboxylic acid containing not more than 18 carbon atoms, or any two of the symbols $R^a$, $R^b$ and $R^c$ together represent carbonyl, lower alkylidene or monocyclic cycloalkylidene, X represents cyano or a group of the formula —C(=O)Z, in which Z represents hydrogen, hydroxy, amino, hydrazino, phenyl, lower alkyl, lower alkoxy or phenyl-lower alkoxy, whereby the phenyl ring can be substituted with nitro, methoxy, methyl or halogen, Y represents hydrogen or has one of the meanings assigned to X, and n is 0 or 1, and a salt of a compound, in which Z is hydroxy, with an alkaline metal, an alkaline-earth metal, ammonia or an organic amine.

2. A compound as claimed in claim 1, wherein $R^b$ and $R^c$ together represent isopropylidene, $R^a$ and $R^d$ represent each hydrogen.

3. A compound according to claim 1 of the formula

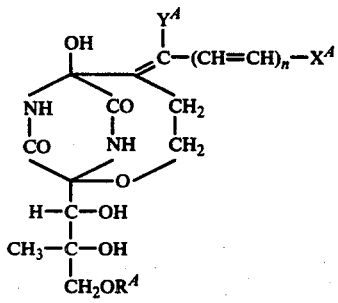

(IA)

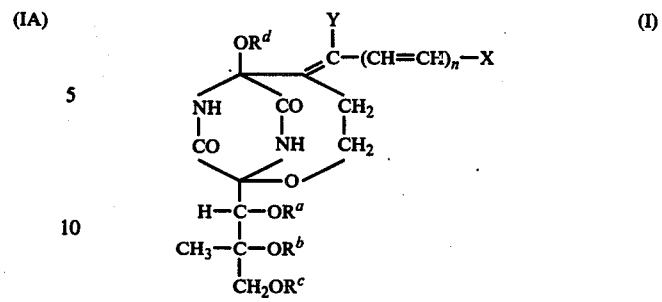

(I)

wherein $X^A$ represents carboxyl, cyano, carbamoyl, carbazoyl or carboxyl esterified with lower alkyl, phenyl-lower alkyl or phenyl-lower alkyl substituted with nitro, methyl, methoxy, chloro or fluoro, $Y^A$ represents hydrogen or has one of the meanings assigned to $X^A$, $R^A$ represents hydrogen or a monovalent acyl group $Ac^A$ derived from formic acid, a lower alkyl hemiester of carbonic acid, a lower alkanecarboxylic acid, benzoic acid or benzoic acid substituted with nitro, methoxy, methyl or halogen and n is 0 or 1, and a physiologically acceptable salt of a compound containing free carboxyl.

4. A compound according to claim 3 of the formula (IA), wherein n is 0, and $R^A$ represents hydrogen.

5. A compound according to claim 1 of the formula

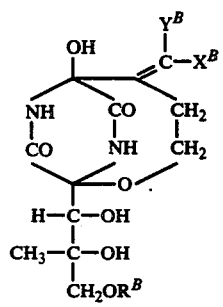

(IB)

wherein $R^B$ represents a lower alkanoyl, benzoyl or hydrogen, $X^B$ represents carboxyl, cyano, lower alkoxycarbonyl, phenyl-lower alkoxycarbonyl or phenyl-lower alkoxycarbonyl substituted with nitro, methoxy, methyl or halogen, $Y^B$ has one of the meanings assigned to $X^B$ or represents hydrogen, and a physiologically acceptable salt of a compound containing free carboxyl.

6. A compound according to claim 5 of the formula (IB), wherein $R^B$ represents a hydrogen atom, $X^B$ represents the cyano, carboxyl or $C_1$-$C_4$-lower alkoxycarbonyl group, and $Y^B$ is hydrogen or has the same meaning as $X^B$, and a physiologically acceptable salt of a compound which contains free carboxyl.

7. A compound according to claim 6 which is selected from the group consisting of bicyclomycin-5a-carboxylic acid, its sodium and potassium salt and its lower alkyl ester.

8. 5a-Methoxycarbonylbicyclomycin.

9. 5a-Cyanobicyclomycin.

10. A process for the manufacture of a 2-oxa-7,9-diazabicyclo[4,2,2]decane compound of the formula wherein each of $R^a$, $R^b$, $R^c$ and $R^d$ individually represents hydrogen, 2-oxaalkyl, 2-oxacycloalkyl or a monovalent acyl $Ac^1$ derived from formic acid, a lower alkyl hemiester of carbonic acid, or from an acyclic or aromatic carboxylic acid containing not more than 18 carbon atoms, or any two of the symbols $R^a$, $R^b$ and $R^c$ together represent carbonyl, a lower alkylidene or a monocyclic cycloalkylidene, X represents cyano or a group of the formula —C(=O)Z, in which Z represents hydrogen, hydroxy, amino, hydrazino, phenyl, lower alkyl, lower alkoxy, or phenyl-lower alkoxy, whereby the phenyl ring can be substituted with nitro, methoxy, methyl or halogen, Y represents hydrogen or has one of the meanings assigned to X, and n is 0 or 1, or a salt of a compound in which Z is hydroxy, with an alkaline metal, an alkaline-earth metal, ammonia or an organic amine, which process comprises reacting a 5-norbicyclomycin-5-one compound of the formula II

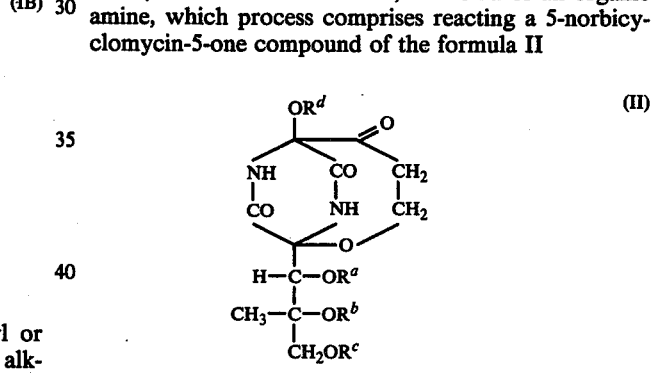

(II)

wherein $R^a$, $R^b$, $R^c$ and $R^d$ are as defined in formula (I), with a compound of the formula

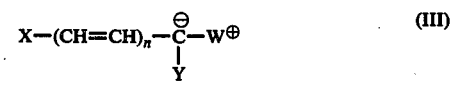

(III)

wherein X, Y and n are as defined in formula (I) and $W^\oplus$ represents a trisubstituted phosphonio group or a diesterified phosphono group together with a cation, and, if desired, in a resultant compound, removing or introducing one or more hydroxyl protective groups $R^a$, $R^b$, $R^c$ and $R^d$ or converting them into other hydroxyl protective groups, and, if desired, converting a resultant compound with a free carboxyl into a salt or a resultant salt into a free carboxylic acid or into another salt.

* * * * *